(12) United States Patent
Bittman et al.

(10) Patent No.: US 6,573,246 B1
(45) Date of Patent: *Jun. 3, 2003

(54) MODIFIED ETHER GLYCEROGLYCOLIPIDS

(75) Inventors: Robert Bittman, Roslyn Heights, NY (US); Ravi K. Erukulla, Plainsboro, NY (US); Andrew C. Peters, Yardley, PA (US); Eric G. Mayhew, Monmouth Junction, NJ (US)

(73) Assignees: The Liposome Company, Inc., Princeton, NJ (US); The Research Foundation of the City University of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/644,470

(22) Filed: Aug. 23, 2000

Related U.S. Application Data

(63) Continuation of application No. 08/722,881, filed on Sep. 26, 1996, now Pat. No. 6,153,736.
(60) Provisional application No. 60/004,398, filed on Sep. 27, 1995.

(51) Int. Cl.⁷ .......................... A61K 31/70; C07H 15/00
(52) U.S. Cl. ............................ 514/25; 514/62; 536/4.1; 536/55.2
(58) Field of Search ................................. 536/4.1, 55.2; 514/25, 62

(56) References Cited

U.S. PATENT DOCUMENTS

| | | | |
|---|---|---|---|
| 4,920,016 A | 4/1990 | Allen et al. | 424/450 |
| 5,219,845 A | 6/1993 | Salari et al. | 514/77 |
| 5,369,097 A | 11/1994 | Salari et al. | 514/77 |
| 5,385,685 A | 1/1995 | Humphreys et al. | 252/174.17 |
| 5,409,902 A | 4/1995 | Carson et al. | 514/23 |
| 5,506,217 A | 4/1996 | Salari et al. | 514/77 |
| 5,756,774 A | 5/1998 | Bittman et al. | 558/161 |

FOREIGN PATENT DOCUMENTS

| | | |
|---|---|---|
| EP | 142333 | 5/1985 |

OTHER PUBLICATIONS

Adam, S. "A new class of potent antiproliferative glycolipids" Chem. Phys. Lipids, vol. 59, pp. 255–261, 1991.*
Bauer et al., "Zur stereoselektiven Synthese von 1–O–Alkyl–3–O–benzyl–sn–glycerolen and 1–O–Alkyl–2–O–methyl–3–O–β–D–glycosyl–sn–glycerolen" Liebigs Ann. Chem. 1991, 765–768.
Bittman et al., "Glycosylated Antitumor Ether Lipids: Synthesis and Growth–Inhibitory Properties". Abstract Book XIXth International Carbvohydrate Symposium, Univ. of California, San Diego, USA Aug. 9–14, 1998.
Lu et al. Oncol. Rep. vol. 1(5): 933–96. Abstract Only, 1994.
Salari et al. Biochem Biophys. Acta. vol. 1134(1): 81–88. Abstract Only. 1991.
Weber et al. Chem. Phys. Lipids, vol. 41(2); 93–100. Abstract Only. 1986.
Byun et al. Tetrahedron Letters, vol. 36(29): 5143–5146, 1995.
Kumar et al. Tertrahedron Letters. vol. 35(4: ) 505–508, 1994.
Weber et al. Biochem. Biophy. Acta. vol. 959: 91–94, 1988.
Guivisdalsky et al., J. Med Chem. 1990, 33, 2614–2641.

* cited by examiner

Primary Examiner—James O. Wilson
Assistant Examiner—Leigh C. Maier
(74) Attorney, Agent, or Firm—Burns, Doane, Swecker & Mathis, L.L.P.

(57) ABSTRACT

This invention provides lipids having: 1) a glycerol backbone; 2) a hydrocarbon chain, preferably saturated and containing 16 or 18 carbon atoms, attached to C-1 of the backbone by an ether linkage, 3) a methyl group attached to C-2 of the backbone, preferably by an ether linkage; and, 4) a sugar attached to C-3 of the glycerol backbone in either the alpha or beta anomeric configuration, the sugar being altered by modification of, or substitution for, one or more of its hydroxyl groups. Also provided herein are ether-lipid-containing compositions, as well as methods of administering such compositions to animals, for example, those afflicted with cancers, as well as various other diseases and disorders.

19 Claims, 1 Drawing Sheet

MODIFIED ETHER GLYCEROGLYCOLIPIDS

This application is a continuation of our U.S. application Ser. No. 08/722,881, filed Sep. 26, 1996, now U.S. Pat. No. 6,153,736, which claims the benefit of U.S. Provisional Application No. 60/004,398, filed Sep. 27, 1995, and now abandoned.

1. Filed of the Invention

This invention is directed to modified ether glyceroglycolipids, compositions containing these compounds, and to the therapeutic administration of these compounds and compositions to animals, including those afflicted with cancers, as well as various other diseases and disorders.

2. Background of the Invention

Etherlipids are amphipathic lipids with ether linkages connecting their hydrocarbons with their molecular backbones, and are synthetic analogs of platelet activating factor ("PAF"; 1-O-2-acetyl-sn-glycero-3-phosphocholine). PAF is an effector believed to be involved in a variety of physiological processes, such as inflammation, immune responses and allergic reactions.

Etherlipids can accumulate in cell membranes, following which the lipids may affect the cells in a number of ways. Cell membrane accumulation can lead to disturbance of membrane lipid organization by a detergent-like activity of etherlipids; membrane structure, and hence, cell stability, can be disrupted by this activity. Phospholipid metabolism can also be disrupted, as the activities of several of the enzymes involved, e.g., CTP: phosphocholine cytidyl transferase, diacylglycerol kinase, sodium/potassium adenosine triphosphate phosphatase, acyl transferases, lysophospholipase, and phospholipases C and D, are inhibited in the presence of etherlipids. Etherlipids can also affect transmembrane signaling pathways, nutrient uptake, cellular differentiation and apoptosis.

Moreover, etherlipids are believed to be cytotoxic to cancer cells, and have been shown to be effective anticancer agents in animals (see, for example, Lohmeyer and Bittman, 1994; Lu et al. (1994a); Lu et al. (1994b); Dietzfelbinger et al. (1993); Zeisig et al. (1993); Berdel (1991); Workman (1991); Workman et al. (1991); Bazill and Dexter (1990); Berdel (1990); Guivisdalsky et al. (1990a); Guivisdalsky et al. (1990b); Powis et al. (1990); Layton et al. (1980): Great Britain Patent No. 1,583,661; U.S. Pat. No. 3,752,886). However, etherlipids are generally not toxic to normal cells. Ether lipids' ability to act selectively on cancer cells is believed to be due to the cancer cells' lack of the alkyl cleavage enzymes necessary for hydrolysis of the lipids; the resulting intracellular lipid accumulation can disrupt the cells' functioning in a variety of ways. Normal cells typically possess these enzymes, and hence, to prevent their intracellular accumulation.

However, not all normal cells contain sufficient levels of alkyl cleavage enzymes to prevent intracellular ether lipid accumulation; cells which do not possess the requisite levels of the enzymes can be subject to the same disruptive effects of ether lipid action as are cancer cells. Red blood cells, for example, lack the requisite alkyl cleavage enzymes, and hence, are also subject to a detergent-like activity of ether lipids. Hemolysis which results from exposure of these cells to ether lipidis having detergent-like activity can be a major drawback to therapeutic use of the ether lipids (see, for example, Houlihan et al., 1995).

A number of different approaches are potentially available for decreasing or eliminating such drug-induced toxicity. One such approach is to incorporate the drugs into lipid-based carriers, e.g., liposomes. Such carriers can buffer drug toxicity, for example, by sequestering the drug in the carrier such that the drug is unavailable for inducing toxicity. Lipid carriers ran also buffer drug-induced toxicity by interacting with the drug such that the drug is then itself unable to interact with the cellular targets through which it exerts its cytotoxic effects. The carriers also maintain the ability of the drugs to be therapeutically effective when released therefrom, e.g., when the carriers are broken down in the vicinity of tumors.

This invention provides etherdipids in which the lipids' phosphate-based headgroups have been replaced with sugar moieties, the sugars themselves having been modified by substitution of one or more of their hydroxyl groups; applicants have found that such modification of etherlipids affords the modified etherlipids beneficial anticancer activity. Certain etherlipid analogues have been mentioned in the art, including O- and S-linked glucose and maltose substitutions of edelfosine's phosphoryicholine group. However, none of these analogues contain sugars modified by replacement of one or more hydroxyl groups.

SUMMARY OF THE INVENTION

Etherlipids of this invention are amphipathic lipid molecules comprising a polyol backbone, a hydrocarbon chain, a methyl group and a modified sugar moiety. The ether lipids have the following structural formula:

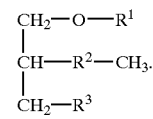

The hydrocarbon, attached to the polyol by way of an ether linkage, is designated herein as "$R^1$" and is a group having the formula $Y^1Y^2$, wherein $Y^1$ is the group $-(CH_2)_{n1}((CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}-$ and $Y^2$ is $CH_3$, $CO_2H$ or $OH$. Preferably, the hydrocarbon is saturated and $Y^1$ is $-C(O)(CH_2)_{n1}$; $Y^2$ is preferably $CH_3$. Most preferably, presently, the hydrocarbon is $-C(O)(CH_2)_{16}CH_3$. The methyl group is attached to the polyol by way of a linkage, designated herein as "$R^2$ which is O, S, NH, or $-NHC(O)-$. Most preferably, $R^2$ is O; accordingly, this invention's glycerol-based etherlipids preferably have a methoxy group at the sn-2 position. The modified sugar attached to the polyol, and designated herein as "$R^3$", has the following formula:

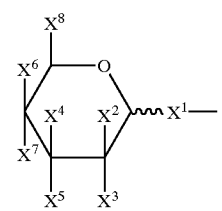

wherein $X^2$, $X^3$, $X^4$, $X^5$, $X^6$ and $X^7$ are either H, OH or a substitution for one of these groups. No more than two of $X^2$, $X^3$, $X^4$, $X^5$ $X^6$ and $X^7$ are OH, and no more than two of $X^2/X^3$, $X^4/X^5$ and $X^6/X^7$ are H/OH or OH/H, when $X^8$ is $CH_2OH$, i.e., when a group other than the OH at C-6 is modified. No more than three of $X^2$, $X^3$, $X^4$, $X^5X^6$ and $X^7$ are OH, and no more than three of $X^2/X^3$, $X^4/X^5$ and $X^6/X^7$ are H/OH or OH/H, when $X^8$ is the group $-COOX^{10}$.

Etherlipids are known to be effective anticancer agents, and can also exert beneficial therapeutic activity against a variety of other diseases and disorders, such as those characterized by inflammation and by microbial infection. Moreover, etherlipids are relatively inactive towards most normal cells. This ability of etherlipids to be selectively cytotoxic to particular target cells is believed to be due to the target cells' lack of the alkyl cleavage enzymes required for hydrolysis of the lipids: normal cells typically possess sufficient levels of these enzymes to prevent intracellular ethedipid accumulation, while cancer cells generally do not. However, some normal cells, e.g., red blood cells, do not possess the requisite alkyl cleavage enzymes in sufficient quantities to prevent etherlipids from accumulating therein to toxic levels; accordingly, ethehipids can be cytotoxic to such cells as well. Etherlipids are incorporated into lipid-based carriers herein such that the etherlipids cannot then be exchanged into cell membranes. Nevertheless, the etherlipids are maintained in a therapeutically effective form within the carrier, and when released therefrom, can act against their intended targets.

DETAILED DESCRIPTION OF THE INVENTION

Figure 1:
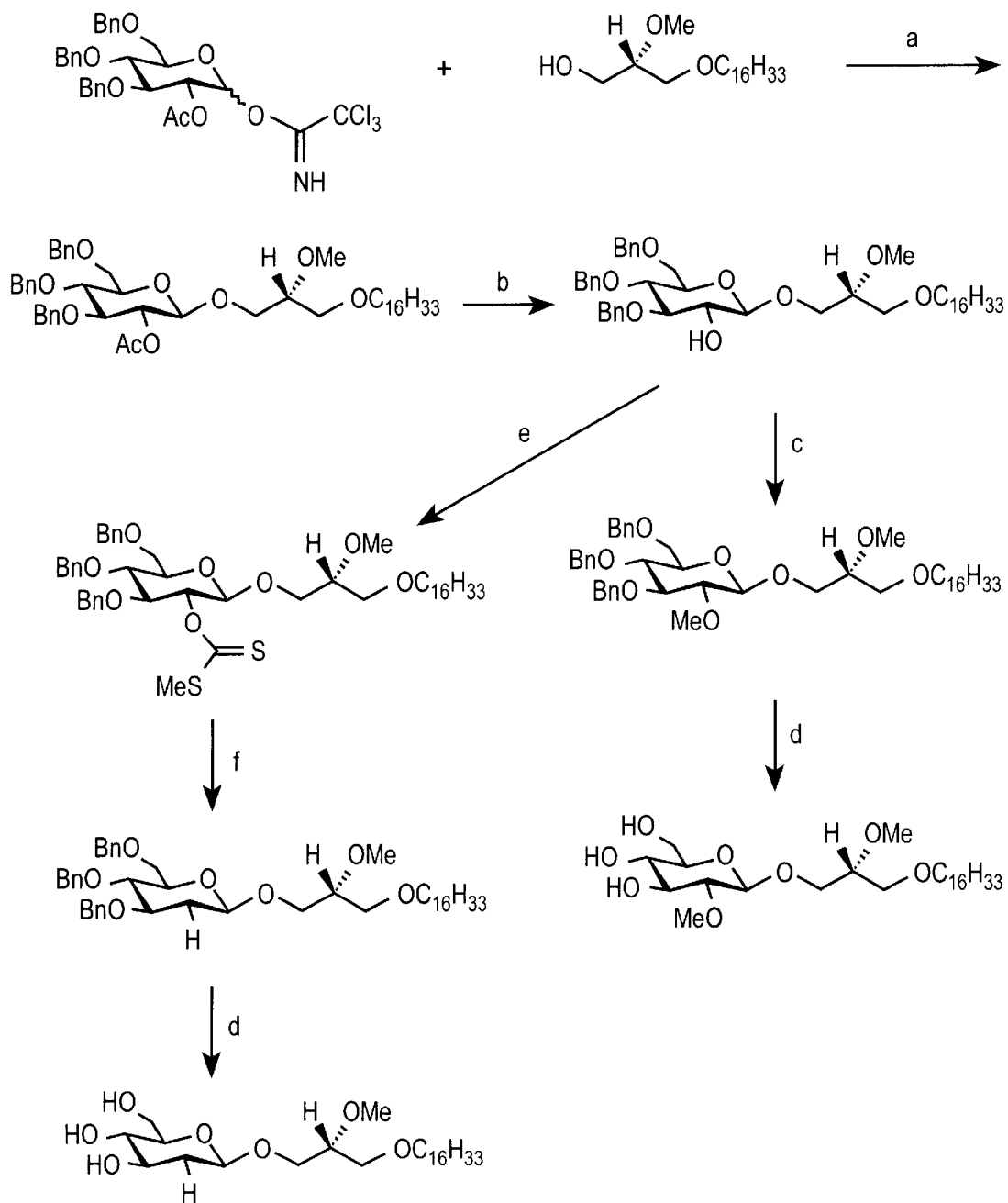
FIG. 1. Reaction scheme for the synthesis of 2'-deoxy-β-D-arabinopyranosyl and 2-O-methyl-β-D-glucopyranosyl modified ether glyceroglycolipids. a: Trimethylsilyl trifluoromethanesulfonate/dichloromethane/molecular sieves 3 angstroms/minus 78 deg. C./10 min. b: $NH_3$—MeOH. c: NaH/DMF/Mel. d: Pd—C/1:1 THF—AcOH, e: $CS_2$/NaH/imidazole/Mel. f: di-N-butyltin oxide/toluene.

This invention provides an etherlipid having the formula:

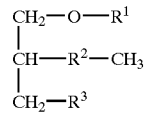

wherein $R^1$ is the group $Y^1Y^2$. $Y^1$ is a group having the formula $—(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}—$. The etherlipid is thus a glycerol-based lipid having a hydrocarbon chain at the sn-1 position, linked to the glycerol backbone by an ether linkage.

The sum of n1+2n2+n3+2n4+n5+2n6+n7+2n8+n9 is an integer if from 3 to 23, n1 is equal to zero or an integer of from 1 to 23, n3 is equal to zero or an integer of from 1 to 20, n5 is equal to zero or an integer of from 1 to 17, n7 is equal to zero or an integer of from 1 to 14 and n9 is equal to zero or an integer of from 1 to 11. Each of n2, n4, n6 and 8 is independently zero or 1. The hydrocarbon is preferably an unsaturated alkyl chain; accordingly, n2, n4, n6 and n8 are each preferably equal to zero, n3, n5, n7 and n9 are each also equal to zero, and $Y^1$ is the group $—C(O)(CH_2)_{n1}$. Alternatively, $Y^1$ can be unsaturated, that is, it can have one or more double bonds; accordingly, at least one of n2, n4, n6 and n8 is then equal to 1. For example, when the unsaturated hydrocarbon has one double bond n2 is equal to 1, n4, n6 and n8 each then being equal to zero, and $Y^1$ is then $—C(O)(CH_2)_{n1}CH=CH(CH_2)_{n3}$.

$Y^2$ is $CH_3$, $CO_2H$ or OH, and is preferably $CH_3$; accordingly, $R^1$ is preferably the group $—C(O)(CH_2)_{n1}CH_3$. More preferably, $R^1$ is $—C(O)(CH_2)_{17}CH_3$.

Etherlipids of this invention also comprise a methyl group, attached to the glycerol backbone by way of a linkage, designated herein as "$R^2$", that is O, S, NH, —NHC(O)—or —OC(O)—. Preferably, $R^2$ is O; accordingly, this invention's glycerol-based etherlipids preferably have a methoxy group at the sn-2 position.

Sugars linked to the third carbon of the glycerol backbone have the following formula:

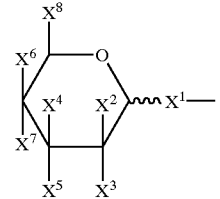

The sugars can be in either the alpha or beta anomeric forms.

Sugars ordinarily have $X^2/X^3$, $X^4/X^5$ and $X^6/X^7$ pairs wherein one member is H and the other is OH. Glucose, for example, has $X^2$ being H and $X^3$ OH, $X^4$ being OH and $X^5$ H, while $X^6$ is H and $X^7$ is OH; in mannose, $X^2$ is OH and $X^3$ is H, $X^4$ is OH and $X^5$ is H, while $X^6$ is H and $X^7$ is OH. $X^8$ is typically $CH_2OH$ in such sugars. This invention provides etherlipids whose headgroups are sugar moieties modified by alteration of, or substitution for, one or more of the sugar hydroxyl groups. No more than two of $X^2$, $X^3$ $X^4$, $X^5$ $X^6$ and $X^7$ are OH's and no more than two of $X^2/X^3$, $X^4/X^5$ and $X^6/X^7$ are H/OH or OH/H when $X^8$ is $CH_2OH$, i.e., when a group other than the OH at C-6 is modified. No more than three of $X^2$, $X^3$, $X^4$, $X^5$ $X^6$ and $X^7$ are OH's, and no more than three of $X^2/X^3$, $X^4/X^5$ and $X^6/X^7$ are H/OH or OH/H when $X^8$ is the group $—COOX^{10}$.

Modifications to sugar molecules according to the practice of this invention are any atom or group of atoms which: 1) can be modified from, or substituted for, a sugar hydroxyl group; and, 2) enhance the cell growth inhibitory activity of a modified sugar-containing etherlipid in comparison to the growth inhibitory activity of the corresponding lipid having the same sugar residue at the sn-3 position, wherein the sugar is not modified at the hydroxyl group. Such modifications include, without limitation, converting a sugar's OH group to H, $NH_2$, $NHCH_3$, $NH(CH_3)_2$, $OCH_3$, $NHC(O)CH_3$, F, Cl, Br, I, $—OP(O)_3^{3-}$ and $—OSO_3^{2-}$. Counterions present when the modified sugar is a salt form are those ions typically used in connection with the groups, e.g., phosphate and sulfate, with which the sugar is modified.

Sugar molecule hydroxyl groups can be modified as described herein, using techniques well known to ordinarily skilled artisans given the teachings of this invention. Comparisons of anticancer activities between different compounds can be accomplished by means also well known to ordinarily skilled artisans given the teachings of this invention. These include, for example, in vitro growth inhibition assays such as those described in Example 18 hereinbelow. Briefly, cells, such as cancer cells, are grown in cultures and the compounds in question are added to the cultures; the concentrations of the compounds required to achieve a certain percentage, e.g., 5%, 10% or 50%, of growth inhibition in the cultures (in comparison to control cultures) are then determined and compared. Compounds which acheive the same level of growth inhibition in a culture at a lower concentration are more effective growth inhibitory agents. Alternatively, an etherlipid can be tested in vivo for anticancer activity, for example, by first establishing tumors in suitable test animals, e.g., immune-deficient mice, administering the etherlipid to the animals and then measuring tumor growth inhibition in the animals and their survival rates. Cells suitable for such in vitro or in vivo testing include, without limitation: murine P388 leukemia, B16 melanoma and Lewis lung cancer cells; human MCF7, ovarian OVCAR-3 and A549 lung cancer cells, as well as other cells generally accepted in the art for such testing.

The sugar can be modifed at any of its OH groups, which can be designated herein as $X^2$, $X^3$, $X^4$, $X^5$, $X^6$ or $X^7$; the sugar can also be modified at the OH group of $X^8$ which, unmodified, is $CH_2OH$. Each of $X^2$ and $X^3$ can be unaltered from the parent sugar so long as at least one of $X^4$, $X^5$, $X^6$, $X^7$ or $X^8$ is then altered; one of $X^2$ and $X^3$ is then H while the other is OH. Alternatively, the OH group at $X^2$ or $X^3$ can be altered as described herein, to give a modified sugar-containing etherlipid; $X^2$ and $X^3$ can then, for example, be H, $NH_2$, $NHCH_3$, $NH(CH_3)_2$, $OCH_3$, $NHC(O)CH_3$, F, or Cl. Each of $X^4$ and $X^5$ can be unaltered from the parent sugar, one then being H while the other is OH; alternatively, the hydroxyl group at $X^4$ or $X^5$ can be altered to give, at $X^4$ or $X^5$ $NH_2$, $NHCH_3$ or $N(CH_3)_2$, $-OPO_3^{3-}$ or $-OSO_3^{2-}$; these include without limitation, sodium and potassium ions, amongst others. Each of $X^6$ and $X^7$ can also be unaltered. When the sugar is a monosaccharide, one of $X^6$ and $X^7$ is then H, while the other is OH; alternatively, when the sugar is a disaccharide, one of $X^6$ and $X^7$ is H while the other is a group having the formula $-OX^9$, wherein $X^9$ is an additional sugar molecule, that is, a tetrose, pentose, a hexose or heptose sugar, linked through an oxygen atom at $X^6$ or $X^7$. Disaccharides have the additional sugar linked through an oxygen at $X^6$ or through an oxygen at $X^7$. One or more hydroxyl groups on the additional sugar can also be modified according to the practice of this invention. $X^8$ is $CH_2OH$ when the sugar is unmodified at the C-6 position, or a group having the formula $-OC(O)X^{10}$ when the sugar is modified at this position, wherein $X^{10}$ is H, $CH_3$ or a group also having the formula $Y^1Y^2$. In preferred embodiments of this invention, $X^1$ is O, $X^4$ is OH, $X^5$ is H, $X^6$ is H, $X^7$ is OH and $X^8$ is $CH_2OH$. Preferably, when $X^2$ is H, $X^3$ is H, $NH_2$ or $-OCH_3$, or when $X^3$ is H, $X^2$ is H or $-OCH_3$.

The etherlipids of this invention can be prepared by a number of means readily practiced by ordinarily skilled artisans given the teachings of this invention for modifying specific groups on sugar molecules. Generally, ethedipid starting material, typically the form of the etherlipid having a phosphorylcholine group at the third position of the glycerol backbone, is glycosylated using a suitable and available glucose donor (which can also be prepared as described below). Sugar OH groups are then modified by known means, typically involving protection/deprotection of unsubstituted groups, to give the desired functional group substitution.

For example, 1-O-hexadecyl-2-O-methyl-sn-glycerol, synthesized from D-mannitol (see Baver et al., 1991), or by the Lewis acid-catalyzed ($BF_3.Et_2O$) regioselective ring opening of (R)-glycidyl arenesulfonates with 1-hexadecanol (see, Guivisdalsky et al., 1991), can be glycosylated to give 1-O-hexadecyl-3-O-protected-sn-glycerol. This 3-O-sn-protected glycerol can be methylated, for example, with diazomethane in the presence of $SiO_2$: followed by deprotection, to give 1-O-hexadecyl-2-O-methyl-sn-glycerol. Alternatively, ordinarily skilled artisans can readily follow a synthetic scheme based, for example, upon asymmetric dihydroxylation of allyl p-methoxyphenyl ether using a chiral phthalazine ligand, such as AD-mix-alpha in a mixture of tert-butanol-water at 0 deg. C., giving 3-O-(p-methoxyphenyl)-sn-glycerol (I; see Vilcheze and Bittman, 1994 and Byun et al., 1994). Selective monoalkylation of I with 1-bromohexadecane, in DMF, via 1,2-O-stannylidene in the presence of CsF (see Nagashima et al., 1987) gives a mixture of sn-1-O-hexadecyl (II) and sn-2-O-hexadecyl glycerols. Following chromatographic separation of these two isomers, II is methylated by treatment with MeI-NaH-DMF; the 3-O-(p-methoxyphenyl) function is then removed with ammonium cerium (IV) nitrate, in aqueous acetonitrile, to give 1-O-hexadecyl-2-O-methyl-sn-glycerol.

Synthesis of analogs with either 2'-deoxy or 2'-O-alkyl functions on monosaccharide residues generally requires that the C-3, C-4 and C-6 protecting groups of the glycosyl donor allow for preferential deprotection of the C-2 glycoside protecting group, resist 2'-O-alkylation and resist deoxygenation. 2-O-Acetyl-3,4,6-tri-O-benzyl-α,β-D-glucopyranosyl trichloroacetimidate and 2-O-acetyl-3,4,6-tri-O-benzyl-α,β-D-mannopyranosyl trichloroacetimidate meet these requirements and can be made, for example, from their respective benzylated 1,2-orthoesters. Briefly, for example, to synthesize 2'-O-acetyl-3,4,6-tri-O-benzyl-α,β-D-glucopyranosyl trichloroacetimidate, the benzylated 1,2-orthoester is acetolized in glacial acetic acid (see Boren et al., 1973, Lemieux et al., 1956 and Trumtel et al., 1989) to give 1',2'-trans-di-O-acetate, the 1-O-acetate function of which is then removed selectively with hydrazine acetate in DMF to give the hemiacetal quantitatively, after aqueous workup. An anomeric mixture of 2-O-acetyl-3,4,6-tri-O-benzyl-α,β-D-glucopyranosyl trichloroacetimidate isomers is obtained by treating the hemiacetal with trichloroacetonitrile-potassium carbonate in dichloromethane, and was then purified by flash chromatography. Synthesis of 2-O-acetyl-3,4,6-tri-O-benzyl-α,β-D-mannopyranosyl trichloroacetimidate involves hydrolysis of the benzylated 1,2-orthoester with acetic acid at room temperature, generally about 25 deg. C., for about 6 hours, followed by treatment of the resulting hemiacetal with trichloroacetonitrile-potassium carbonate in dichloromethane.

Functionalization of the C-2' position of the monosaccharide attached to the etherlipid can, for example, be carried out according to the reaction scheme depicted in FIG. 1 and described below. Briefly, the 2-O-acetyl functions of 1-O-hexadecyl-2-O-methyl-3-O-(2'-O-acetyl-3',4',6'-tri-O-benzyl-β-D-glucopyranosyl)-sn-glycerol and 1-O-hexadecyl-2-O-methyl-3-O-(2'-O-acetyl-3',4',6'-tri-O-benzyl-α-D-mannopyranosyl)-sn-glycerol are quantitatively removed by $NH_3$/MeOH aminolysis, followed by methylation of the 2' hydroxy group with NaH-DMF-MeI to give 1-O-hexadecyl-2-O-methyl-3-O-(2'-O-methyl-3',4',6'-tri-O-benzyl-β-D-glucopyransoyl)-sn-glycerol or 1-O-hexadecyl-2-O-methyl-3-O-2-O-methyl-3',4',6'-tri-O-benzyl-α-D-mannopyransoyl)-sn-glycerol, respectively. The O-benzyl protecting groups are then removed in 1:1 THF-HOAc using Pd-C, under a balloon pressure of hydrogen, to give 2-O-methyl-β-D-glycopyransoyl and 2-O-methyl-α-D-mannopyransoyl etherlipids. Low molecular weight impurities can be removed from such compounds by filtration, for example, through lipophilic Sephadex LH-20 using methanol.

Further useful synthetic techniques include radical xanthate reduction, which is a procedure commonly used to deoxygenate carbinols. Alcohols can be converted to the corresponding xanthates, for example, by treatment in tetrahydrofuran (THF) with sodium hydride, carbon disulfide and a catalytic amount of imidazole, followed by reaction with MeI. The xanthates can the be converted to the corresponding 2'-deoxy-glycosides by radical reduction with dibutyltin oxide (see Barton et al., 1975; and Hartwig, 1983) in the presence of azobisisobutyronitrile (AIBN); confirmation of the reduction can be made by NMR spectroscopy. The contents of the above cited disclosures of reactions and synthetic schemes for the modification of sugar molecule OH groups are incorporated herein by reference.

Also provided herein is a composition comprising an etherlipid of this invention; the composition preferably also comprises a pharmaceutically acceptable medium, which are media generally intended for use in connection with the administration of active ingredients to animals, and are formulated according to a number of factors well within the purview of the ordinarily skilled artisan to determine and account for. These include, without limitation: the particular active ingredient used, its concentration, stability and intended bioavailability; the disease, disorder or condition being treated with the composition; the subject, its age, size and general condition; and the composition's intended route of administration (see, for example, J. G. Naim, in: *Remington's Pharmaceutical Science* (A. Gennaro, ed.), Mack Publishing Co., Easton, Pa., (1985), pp. 1492–1517, the contents of which are incorporated herein by reference). Pharmaceutically acceptable media include, without limitation: solids, such as pills. capsules and tablets; gels; excipients; and aqueous or nonaqueous solutions. Typical pharmaceutically acceptable media used in parenteral drug administration include, for example, D5W, an aqueous solution containing 5% weight by volume of dextrose, and physiological saline.

Etherlipid-containing compositions provided herein preferably also comprise a lipid carrier with which the etherdipid is associated. "Lipid cariers" are hydrophobic or amphipathic molecules suitable for administration to animals, and include, without limitation: fatty acids, phospholipids, micelles, lipoproteins, nonliposomal lipid-based complexes and liposomes. Preferably, the lipid carrier is a liposome, which comprises one or more bilayers of lipid molecules, each bilayer encompassing an aqueous compartment. The amphipathic lipid molecules which make up lipid bilayers comprise polar (hydrophilic) headgroups and nonpolar (hydrophobic) hydrocarbon chains. The polar groups can be phosphate-, sulfate- or nitrogen-based groups, but are preferably phosphate groups such as phosphorylcholine, phosphorylethanolamine, phosphorylserine, phosphorylglycerol or phosphorylinositiol. The hydrocarbons generally comprise from 12 to 24 carbon atoms, and can be saturated (e.g., myristic, lauric, palmitic, or stearic acid), or unsaturated (e.g., oleic, linolenic or arachidonic acid). Liposomal bilayers can also include sterols, such as cholesterol, other lipids and nonlipid molecules.

"Association" between an etherlipid and a lipid carrier is by way of a number of influences, such as Van der Waals forces, generally known to operate between hydrophobic molecules in an aqueous environment. Means of determining the stability of such associations, for example, by determining the percentage of etherlipid recoverable with phosphorous when the lipid carrier comprises a phospholipid, are well known to, and readily practiced by, ordinarily skilled artisans given the teachings of this invention.

Lipid carrier-based formulations can enhance the therapeutic index of an associated etherlipid, by buffering the lipid's toxicity-causing potential while maintaining or enhancing its therapeutic efficacy, for example, by increasing the amount of the etherlipid-lipid carrier association reaching the intended site of therapeutic action. Preferred means for doing so include increasing the length of time in which the etherlipid-lipid carrier association remains in the circulation of animals to which it has been administered. In the case of cancer treatment, for example, increasing circulatory half-life allows more of the administered material to reach tumors, which tend to have an increased amount of vasculature in comparison to surrounding tissue; this vasculature also tends to be more leaky than that found in healthy tissue, meaning that etherlipid-lipid carrier associations can readily reach leak out into surrounding tumor tissue.

Preferred means for enhancing etherlipid-lipid carrier circulation is by incorporating a "headgroup-modified lipid" into the lipid carrier. Headgroup-modified lipids, e.g., phosphatidylethanolamines ("PE's"), generally comprise polar groups derivatized by attachment thereto of a moiety, e.g., dicarboxylic acids such as succinic and glutaric acids, which can inhibit the binding of serum proteins to the carriers so that the pharmacokinetic behavior of the carriers is altered (see, e.g., Blume et al., Biochim. Biophys. Acta. 1149:180 (1993); Gabizon et al., Pharm. Res. 10(5):703 (1993); Park et al. Biochim. Biophys Acta. 1108:257 (1992); Woodle et al., U.S. Pat. No. 5,013,556; and Allen et al., U.S. Pat. Nos. 4,837,028 and 4,920,016, the contens of which are incorporated herein by reference). The amount of the headgroup-modified lipid incorporated into the lipid carrier generally depends upon a number of factors well known to the ordinarily skilled artisan, or within his purview to determine without undue experimentation, given the teachings of this invention. These include, but are not limited to: the type of lipid and the type of headgroup modification; the type and size of the carrier; and the intended therapeutic use of the formulation. Typically, from about 5 to about 20 mole percent of the lipid in a headgroup-modified lipid-containing lipid carrier is headgroup-modified lipid.

Further provided herein is a method of administering an etherlipid to an animal, which comprises administering an etherlipid-containing composition of this invention to the animal. The animal is preferably a human, and administration is preferably intravenous, but can also be by any other means generally accepted for administration of therapeutic agents to animals. Etherlipid-containing compositions provided herein can be administered prophylactically or therapeutically to animals at risk of, or afflicted with, various diseases and disorders which include, without limitation, cancerous, inflammatory and infectious conditions.

Cancers, e.g., brain, breast, lung, colon, ovarian, prostate, liver or stomach cancers, and carcinomas, sarcomas and melanomas, can be treated with the etherlipid-containing compositions of this invention. The compositions are particularly useful for the treatment of drug-resistant cancers, i.e., forms of a cancer resistant to one or more drugs, e.g., adriamycin, commonly used to treat the cancer. Preferably, compositions used to treat cancers comprise, in addition to an etherlipid, a lipid carrier, more preferably, a liposome. Most preferably, the liposome is a unilamellar liposome having an average diameter of from about 100 nm to about 200 nm.

Animals treated for cancers according to the practice of this invention are given an anticancer effective amount of an etherlipid. "Anticancer effective amounts" of an etherlipid are any amount of the etherlipid effective to ameliorate, lessen, inhibit or prevent the establishment, growth, metastasis, or invasion of a cancer. Generally, the anticancer effective amount of the etherlipid is at least about 0.1 mg of the etherlipid per kg of body weight of the animal to which the etherlipid-containing composition is administered. Typically, the anticancer effective amount of the etherlipid is from about 0.1 mg per kg of body weight of the animal to about 1000 mg per kg; preferably, the anticancer effective amount is from about 1 mg of the lipid per kg to about 200 mg per kg. Within these ranges, etherlipid doses are chosen in accordance with a number of factors, e.g., the age, size and general condition of the subject, the cancer being treated and the intended route of administration of the lipid, well known to, and readily practiced by, ordinarily skilled artisans given the teachings of this invention.

Etherlipid treatment can follow a variety of accepted chemotherapeutic regimens, and can include administration of an anticancer effective amount in segments over a suitable period of time, or repeated administrations of an anticancer effective amount, each dosing being separated by a suitable period of time. Additional bioactive agents, i.e., bioactive agents in addition to the etherlipid, can be administered to the animal in accordance with the practice of this invention, either concurrently with, or separately from etherlipid administration, and either as a component of the same, or a different, composition. "Bioactive agents" are compounds or compositions of matter having biological activity on animal cells in vitro or when administered to an animal; bioactive agents can have therapeutic and/or diagnostic activity. Such agents include, but are not limited to, antimicrobial, anti-inflammatory and anticancer agents, as well as radioactive agents, enzymes isotopes and dyes.

This invention will be better understood from the following Examples. However, those of ordinary skill in the art will readily understand that these examples are merely illustrative of the invention as defined in the claims which follow thereafter.

EXAMPLES

Example 1
Materials and Methods

Silica gel GF TLC plates of 0.25-mm thickness (Analtech, Newark, Del.) were used to monitor reactions, with visualization by charring using 10% sulfuric acid in ethanol and/or short wavelength ultraviolet light. Flash chromatography was carried out with silica gel 60 (230–400 ASTM mesh) of E. Merck (purchased from Aldrich), isocratically unless otherwise stated. $^1$H NMR spectra were recorded on IBM-Bruker WP-200 and AMX400 spectrometers, at 200 and 400.13 MHz, respectively, in $CDCl_3$ solutions—chemical shifts are in parts per million from tetramethylsilane as the internal standard; $^{13}$C-NMR spectra were recorded at 75 MHz and 100.57 MHz, respectively—$^{13}$C chemical shifts are given by assigning 77.0 ppm for the central line of $CDCl_3$. Optical rotations were measured at 20±2 deg. with a JASCO DIP-140 digital polarimeter, in a cell of 1-dm path length; 1% solutions in chloroform were used, unless otherwise stated. The melting points are uncorrected.

Trity chloride was obtained from Aldrich. Zinc chloride was obtained from Fluka. Dichloromethane was dried over $P_2O_5$ and distilled just before use, or refluxed over calcium hydride and distilled under a positive nitrogen pressure before use; tetrahydrofuran was refluxed over sodium benzophenone ketone and distilled before use; methanol was refluxed over $Mg(OMe)_2$ and distilled before use; toluene was distilled and then redistilled from calcium hydride before use; anhydrous N, N-dimethyl formamide (DMF) was acquired from Janssen Chimica. Solid synthons were dried under vacuum (0.2 mm Hg), and all reactions were carried out under dry nitrogen using air-sensitive glassware (greaseless vacuum/gas manifold). Nitrogen gas was dried through a drying tower of granulous anhydrous calcium chloride. Molecular sieves of 3 angstroms were dried at 150 deg. C., under vacuum, over $P_2O_5$ for 12 hours, and stored under vacuum over $P_2O_5$.

Human epithelial cancer cell lines were grown from frozen stocks originally obtained from the ATCC, in media commonly used for growing these cells in culture. For example, A549 cells (non-small cell lung adenocarcinoma) were cultured in Ham's F-12 medium, T84 cells (colon carcinoma) were cultured in a 1:1 mixture of F-12 and DMEM while MCF-7 (breast adenocarcinoma) and A427 (large cell lung carcinoma) cells were cultured in DMEM. The media were supplemented with 10% fetal bovine serum, penicillin (50 U/ml), streptomycin (50 microgram/ml) and fungizone (0.5 microgram/ml). OVCAR-3 cells (ovarian adenocarcinoma) were cultured in RPMI 1640 medium supplemented with 20% FBS and 10 microgram/ml insulin.

Cells were subcultured into 24-well plates and the cell number was monitored daily. When the cells were in log phase, the media was replaced with one containing the required drug concentration, and the cells were incubated for 72 h. The increase in cell numbers relative to control wells (without any drug) was determined after the incubation. Stock solutions of the drugs (30 micromolar) were prepared in ethanol and stored at −20 deg. C. Etherlipid solutions (30 micromolar) in the appropriate media were prepared fresh on the day of the experiment and serially diluted to give the required concentrations. The final concentration of ethanol in all wells was 0.1% (v/v).

Example 2
Synthesis of 1-O-hexadecyl-2-O-methyl-sn-gylcerol

To a solution of 1-O-hexadecyl-2-O-methyl-3-O-p-methoxyphenyl)-sn-glycerol (1.0 g, 2.3 mmol) in 4:1 acetonitrile-water (21 ml) was added ammonium cerium(IV) nitrate (2.9 g, 5.5 mmol) at 0 deg. C., with vigorous stirring. The resulting mixture was warmed to room temperature, and stirred for one hour, following which TLC (4:1 hexane:ethyl acetate) showed complete conversion of the starting material to 1-O-hexadecyl-2-O-methyl-sn-glycerol. The reaction was quenched by addition of 1.0 g sodium sulfite.

The resulting mixture was diluted with ethyl acetate, and the organic solution was washed with water, brine, and dried with sodium sulfate; it was then filtered, and the filtrate evaporated. The residue was purified by column chromatography (6:1 hexane:ethyl acetate) to give 1-O-hexadecyl-2-O-methyl-sn-glycerol (0.853 g, 94%) as a low melting point white solid. $[\alpha]_D$-9.5 deg.

Example 3
Synthesis of 1-O-hexadecyl-2-O-methyl-3-O-(2'-acetamido-2'-deoxy-3',4',6'-tri-O-acetyl-β-D-glucopyranosyl)-sn-glycerol To a solution of 2-acetamido-2-deoxy-3,4,6-tri-O-acetyl-α-D-glucopyranosyl chloride (219.4 mg, 0.6 mmol), 1-O-hexadecy-2-O-methyl-sn-glycerol (100 mg, 0.3 mmol), and trityl chloride (83.6 mg, 0.3 mmol) were added 41.2 mg (0.3 mmol) of zinc chloride in dry dichloromethane (5 ml; see Kumar et al., 1994). The reaction mixture was stirred for 4 h at room temperature, and reaction progress was monitored by TLC analysis, in ethyl acetate. The reaction mixture was diluted with ethyl acetate (50 ml), washed with 5% aqueous sodium bicarbonate solution, washed with water, dried over sodium sulfate, and concentrated under reduced pressure. The residue was purified by flash chromatography (elution with hexane/ethyl acetate 1:1), giving 140 mg (70%) of 1-O-hexadecyl-2-O-methyl-3-O-(2'-acetamido-2'-deoxy-3', 4',6'-tri-O-acetyl-β-D-glucopyranosyl)-sn-glycerol as a white solid; $R_f$. 0.54 (ethyl acetate); $[\alpha]_D$25 −1.31 deg. (c5.6, $CHCl_3$); $^1$H NMR (200 MHz, $CDCl_3$) δ0.80 (t, 3H, J=5.96 Hz, $CH_3$), 1.25 (br, 26H, $(CH_2)_{13}CH_3$), 1.45 (2H, $OCH_2CH_2$), 1.87, 1.95, 2.01 (s, 12H, OAc, and NAc), 3.32–3.41 (m, 8H, with a singlet at d 3.36, CH$_2$OCH$_2$C$_{15}$H$_{31}$, CH$_3$OCH), 3.63 (m, 3H, H-5 and OCH$_2$), 3.81 (m, 1H, H-2), 4.02 (dd, 1H, H-6a), 4.08 (dd, 1H, J=4.57 Hz, H-6b), 4.60 (d, 1H, J=8.34 Hz, H-1), 5.05 (t, 1H, J=9.50 Hz, H-4), 5.17 (t, 1H, J=9.83 Hz, H-3), 5.84 (d, 1H, J=8.51 Hz, NH).

Example 4
Synthesis of 1-O-hexadecyl-2-O-methyl-3-O-(2'-acetamido-2'-deoxy-β-D-glucopyranosyl)-sn-glycerol 1-O-Hexadecyl-2-O-methyl-3-O-(2'-acetamido-2'-deoxy-3',4',6'-tri-O-acetyl-β-D-glucopyranosyl)-sn-glycerol (140 mg, 0.21 mmol), prepared aacording to the procedures of Example 3 as described above, was dissolved in 3 ml of 0.25 N methanolic KOH, and the mixture was stirred for 2 h at room temperature. The reaction mixture was neutralized with saturated aqueous ammonium chloride solution and extracted with chloroform (10 ml). The chloroform layer was dried over MgSO$_4$ and concentrated under reduced pressure and the residue was purified by flash chromatography (elution with 10% methanol in chloroform), giving 109 mg (96%) of 1-O-hexadecyl-2-O-methyl-3-O-(2'-acetamido-2'-deoxy-β-D-glucopyranosyl)-sn-gycerol as a white solid; mp 150–153 deg. C.; R$_f$ 0.56 (CHCl$_3$—CH$_3$OH 4:1); [α]$_D^{25}$ −2.26 deg. C. (c 5.25, CHCl$_3$—CH$_3$OH); $^1$H NMR (200 MHz, CDCl$_3$ and a few drops of CD$_3$OD) δ0.80 (t, 3H, J =6.33 Hz, CH$_3$), 1.25 (br, 26H, (CH$_2$)$_{13}$CH$_3$), 1.56 (2H, OCH$_2$CH$_2$), 2.01 (s, 3H, NAc), 3.23–3.83 (m, 19H, with a singlet at δ3.45, CH$_2$OCH$_2$C$_{15}$H$_{31}$, CH$_3$OCH, OCH$_2$ and —CHO-'s of sugar moiety), 4.43 (d, 1H, J=6.84 Hz, H-1), 7.51 (d, 1H, J=8.51 Hz, NH).

Example 5
Synthesis of 1-O-hexadecyl-2-O-methyl-3-O-(2'-amino-2'-deoxy-β-D-glucoryranosyl)-sn-glycerol 1-O-Hexadecyl-2-O-methyl-3-O-(2'-acetamido-2'-deoxy-β-D-glucopyranosyl)-sn-glycerol (24 mg, 45.3 μmol), prepared as described above, was dissolved in 2 ml of 2 N ethanolic KOH. The mixture refluxed for 4 h, cooled, and then neutralized with saturated aqueous ammonium chloride solution; the product was extracted with chloroform. The chloroform layer was dried over MgSO$_4$ and concentrated under reduced pressure; the residue was purified by flash chromatography (elution with 20% methanol in chloroform), giving 18 mg (82%) of 1-O-hexadecyl-2-O-methyl-3-O-(2'-amino-2-deoxy-β-D-glucopyranosyl)-sn-glycerol as a white solid. R$_f$ 0.28 (CHCl$_3$—CH$_3$OH 4:1); [α]$_D^{25}$ −14.40 deg. (c 7.5, CHCl$_3$/CH$_3$OH 1:1 (v/v); $^1$H NMR (200 MHz, CDCl$_3$ and a few drops of CD$_3$OD) δ0.85 (t, 3H, J=6.34 Hz, CH$_3$), 1.23 (br, 26H, (CH$_2$)$_{13}$CH$_3$), 1.53 (2H, OCH$_2$CH$_2$), 3.40–3.91 (m, 20H, with a singlet at d 3.45, CH$_2$OCH$_2$C$_{15}$H$_{31}$, CH$_3$OCH, OCH$_2$, and —CHO-'s of sugar moiety) 4.82 (br s, 2H, NH$_2$). HRMS (FAB, MH$^+$). Calculated for C$_{26}$H$_{54}$NO$_7$: 492.3900. Found 492.3899.

Example 6
Synthesis of 1-O-hexadecyl-3-O-(p-methoxyphenyl)-sn-gylcerol (I) and 2-O-hexadecyl-3-O-(p-methoxyphenyl)-sn-glycerol (II)

A mixture of 3-O-(p-methoxyohenyl)-sn-glycerol (0.737 g, 3.7 mmol) and di-n-butyltin oxide (1.11 g, 4.46 mmol) in dry methanol (10 ml) was refluxed, with stirring, until the oxide was dissolved. The solvent was evaporated, and the solid was dried under vacuum for 3 hours; the dried solid was then dissolved in DMF (30 ml) and cesium flouride (1.5 g) and 1-bromohexane (1.57 ml, 5.13 mmol) were added. The resulting mixture was stirred at room temperature until TLC (4:1 hexane-ethyl acetate) indicated that the reaction was complete. Ethyl acetate (20 ml) and water (0.5 ml) were then added, and the mixture was stirred for 30 minutes. The resulting white solid was filtered, and the solvent evaporated to give a crude mixture of I and II. This mixture of monoalkylated products was separated by column chromatography.

(I): 1.42 g (90%). [α]$_D$ $^1$H-NMR: δ6.84–6.78 (m, 4H, Ph), 4.13 (m, 1H, H-2), 4.03–3.95 (m, 2H, H-3a, H-3b), 3.76 (s, 3H, OCH$_3$), 3.57 and 3.54 (dd, 2H, J$_{1a,1b}$=12 Hz, J$_{1,2}$=4.0 Hz, H-1a, H-1b), 3.46 (t, 2H, J=4.0 Hz, OCH$_2$), 2.56 (1H, OH), 1.6 (t, 2H, J=6.0 Hz, CH$_2$), 1.25 (s, 26H, CH$_2$), 0.88 (t, 3H, J=6.0 Hz, CH$_3$). $^{13}$C-NMR: δ115.89, 114.99 (Ar), 72.02 (OCH$_2$), 71.97 C-1), 70.16 (C-3), 69.53 (C-2), 56.02 (OCH$_3$).

(II): (76%). $^1$H-NMR: δ6.87–6.80 (m, 4H, Ph), 3.89 (d, 2H, J=4.4 Hz), 3.73–3.48 (m, 5H, H-1a, H-1b, H-2, H-3a, H-3b), 3.63 (s, OCH$_3$), 2.25 (1H, OH), 1.6 (t, 2H, J=6.0 Hz, CH$_2$), 1.25 (s, 26H, CH$_2$), 0.88 (t, 3H, J=6.0 Hz, CH$_3$). $^{13}$C-NMR: δ115.93, 114.99 (Ar), 78.69 (C-2), 62.75 (C-1), 56.03 (OCH$_3$).

Example 7
Synthesis of 1-O-hexadecyl-2-O-methyl-3-O-(p-methoxyphenyl)-sn-glycerol General procedure for alcohol methylation: sodium hydride (2.5 mmol), in dry DMF, was added portionwise at zero deg. C. to stirred alcohol solutions (1 mmol). The resulting mixture was stirred for 30 minutes, and methyl iodide was then added (2.5 mmol). The reaction was stirred at room temperature; once complete, methanol was added at zero deg. C. to quench excess sodium hydride. Solvent was then evaporated under vacuum, and the residue was dissolved in ethyl acetate. The organic solution was washed with water and brine, dried (Na$_2$SO$_4$), filtered and evaporated.

1-O-Hexadecyl-3-O(p-methoxyphenyl)-sn-glycerol (1.2 g, 2.84 mmol) was methylated to give 1-O-hexadecyl-2-O-methyl-3-O-(p-methoxyphenyl)-sn-glycerol as a white solid (1.2 g) in 97% after column purification. [α]$_D$−6.9 deg.; $^{13}$C-NMR: δ115.90, 114.99 (Ar), 78.8 (C-2), 72.02, 71.98, 70.20 (C-1, C-3, OCH$_2$), 57.88, 56.02 (OCH$_3$).

Example 8
Synthesis of 2-O-acetyl-3,4,6-tri-O-benzyl-α, β-D-glucopyranosyl trichloroacetimidate To a solution of 1,2-di-O-acetyl-3,4,6-tri-O-benzyl-β-D-glucopyranose (1 g, 1.87 mmol) in dry DMF (10 ml) 0.213 g (2.32 mmol) of hydrazine acetate was added. This mixture was stirred under nitrogen for 4 hours. After this time, TLC (4:1 hexaneethyl acetate) showed that the reaction was complete. The mixture was then diluted with ethyl acetate, and washed with water and brine. The organic layer washed (sodium sulfate), filtered and then evaporated to give the crude hemiacetal quantitatively, the crude hemiacetal, pure enough to continue with, was then dried under vacuum for 4 hours and dissolved in dry dichloromethane (30 ml). Trichloroacetonitrile (0.231 ml) and anhydrous potassium carbonate (1.22 g) were added, and the resulting mixture was stirred for 3 hours under nitrogen. TLC (4:1 hexane-:ethyl acetate) showed traces of the crude hemiacetal, and the faster-running 2-O-acetyl-3,4,6-tri-O-benzyl-α,β-D-glucopyranosyl trichloroacetimidate. The reaction was quenched by filtration of the inorganic base through a pad of Celite 545, and the solvent was evaporated. Crude 2-O-acetyl-3,4,6-tri-O-benzyl-α, β-D-glucopyranosyl trichloroacetimidate was then purified through a short column using 8:1 hexane:ethyl acetate to give the glucosyl donor 2-O-acetyl-3,4,6-tri-O-benzyl-α,β-D-glucopyranosyl trichloroacetimidate in 85% yield. $^1$H-NMR: δ8.63 (s, 0.46H, NH), 8.56 (s, 0.56H, NH), 7.32–7.15 (m, 15H, 3Ph), 6.52 (d, 0.53H, $J_{1,2}$ =3.5 Hz, H-1a), 5.74 (d, 0.46H, $J_{1,2}$=8.0 Hz, H-1$_b$), 5.29 (dd, 0.46H, $J_{2,3}$=9.4 Hz, H-2b isomer), 5.09 (dd 0.53H, $J_{2,3}$=10.0 Hz, H-2a isomer), 1.99 (s, CH$_3$CO).

Example 9
Synthesis of 2-O-acetyl-3,4,6-tri-O-benzyl-α,β-D-mannopyranosyl trichloroacetimidate The benzylated 1,2-orthoester (3.0 g), prepared as described above, was hydrolyzed in HOAc 80% (50 ml) at room temperature for 6 hours. After this time, TLC (2:1 hexane:ethyl acetate) showed complete conversion of the ester into a slower moving material. Acetic acid was coevaporated with toluene, under vacuum, to give the pure hemiacetal quantitatively (3.0 g); the crude hemiacetal was then dried overnight, under vacuum, following which it was treated with acetonitrile-potassium carbonate to give 2-O-acetyl-3,4,6-tri-O-benzyl-α,β-D-mannopyranosyl trichloroacetimidate in 96% (3.8 g). $^1$H-NMR: δ8.71 (s, NH), 8.63 (s, NH), 7.35–6.78 (m, 15H, 3Ph), 6.29 (d, H-1b), 5.89 (d, H-1a), 5.49 (dd, H-2), 4.89–4.47 (m), 4.06–3.68 (m), 2.18 (s, 3H, CH$_3$).

Example 10
Glycosylation of 1-O-hexadecyl-2-O-methyl-sn-glycerol with 2-O-acetyl-3,4,6-tri-O-benzyl-α,β-D-glucooyranosyl trichloroacetimidate and 2-O-acetyl-3,4,6-tri-O-benzyl-α,β-D-mannopyranosyl trichloroacetimidate A mixture of the glucosyl donor (1.4 micromolar) and 1-O-hexadecyl-2-O-methyl-sn-glycerol (1.3 micromolar), prepared as described above, in 30 ml of anhydrous dichloromethane was stirred under dry nitrogen, with molecular seives 3 Å for 20 minutes at room temperature. The mixture was cooled at −78 deg. C., and trimethylsilyl trifluoromethanesulfonate (50 micromoles. 0.035 eq.) was added. In every case, the reaction was complete in 10 minutes. The Lewis acid was neutralized at room temperature with triethylamine (20 microliters), the solvent was evaporated, and the crude 1,2-trans-glycopyranosides were purified by column chromatography.

Example 11
Synthesis of 1-O-hexadecyl-2-O-methyl-3-O-(2'-O-acetyl-3',4',6'-tri-O-benzyl-β-D-glucopyranosyl)-sn-glycerol 1-O-Hexadecyl-2-O-methyl-sn-glycerol (433.3 mg, 1.3 mmol) prepared as described above, was glucosylated with 2-O-acetyl-3,4,6-tri-O-benzyl-α, β-D-glucopyranosyl trichloroacetimidate (930 mg, 1.4 mmol) to give 1-O-Hexadecyl-2-O-methyl-3-O-(2'-O-acetyl-3',4',6'-tri-O-benzyl-β-D-glucopyranosyl)-sn-glycerol in 76% yield (805 mg). $[α]_D$ −8.5 deg. $^1$H-NMR: δ7.32–7.15 (m, 15H, 3PhCH$_2$) 4.99 (dd, 1H, $J_{1',2a'}$=2.5 Hz, $J_{1',2e'}$=−1.0 Hz, H-1'), 3.93 (m, 1H, H-5'), 3.44 (s, 3H, OCH$_3$), 2.15 (ddd, 1H, $J_{2e',3'}$=4.7 Hz, $J_{2e',2a'}$=11.5 Hz,H-2e'), 1.7 (ddd, 1H, H-2a', 1.25 (s, 26H, CH$_2$), 0.87 (t, 3H, CH$_3$). $^{13}$C-NMR: δ98.05 (C-1'), 79.33, (C-5'), 62.07 (C-6'), 57.94 (OCH$_3$), 37.36 (C-2'), 31.90, 29.64, 29.48, 29.31, 26.06, 22.67 (CH$_2$), 14.06 (CH$_3$).

Example 12
Synthesis of 1-O-hexadecyl-2-O-methyl-3-O-(2'-O-acetyl-3',4',6'-tri-O-benzyl-α-D-mannopyranosyl)-sn-glycerol 1-O-Hexadecyl-2-O-methyl-sn-glycerol (871 mg, 2.6 micromolar) was glucosylated with 2-O-acetyl-3',4',6'-tri-O-benzyl-α,β-D-mannopyranosyl trichloroacetimidate (1.90 g, 2.9 mmol), prepared as described above, to give 1-O-hexadecyl-2-O-methyl-3-O-(2-O-acetyl-3',4',6'-tri-O-benzyl-α-D-mannopyranosyl)-sn-glycerol in 87% yield (1.83 9). $[α]_D$ +37.5 deg. $^1$H-NMR: δ7.33–7.12 (m, 15H, 3PhCH$_2$), 5.37 (dd, 1H, $J_{2',3'}$=2.7 Hz, H-1'), 4.86 and 4.49 (2d, 2H, J=12 Hz, CH$_2$Ph), 2.14 (s, 3H, CH$_3$CO), 1.54 (t, 2H, J=6 Hz), 1.25 (s, 26H), 0.87 (t, 3H). $^{13}$C-NMR: δ170.39 (CO), 138.50, 132.29, 128.28, 127.55 (Ph), 98.17 (C-1'), 58.07 (CH$_3$O), 31.90, 29.51, 26.10, 21.07 (CH$_2$), 14.07 (CH$_3$).

Example 13
Deacetylation of 1-O-hexadecyl-2-O-methyl-3-O-(2'-O-acetyl-3',4',6'-tri-O-benzyl-β-D-glucopyranosyl)-sn-gylcerol and 1-O-hexadecyl-2-O-methyl-3-O-(2'-O-acetyl-3',4',6'-tri-O-benzyl-α-D-mannopyranosyl)-sn-gylcerol 1-O-Hexadecyl-2-O-methyl-3-O-(2'-O-acetyl-3',4',6'-tri-O-benzyl-β-D-glucopyranosyl)-sn-gylcerol and 1-O-hexadecyl-2-O-methyl-3-O-(2'-O-acetyl-3',4',6'-tri-O-benzyl-α-D-mannopyranosyl)-sn-glycerol, prepared as described above, were deacetylated at room temperature with dry ammonia gas dissolved in dry methanol in 15 minutes. This reaction was quantitative and gave very pure products. Methanol was evaporated, and the resulting alcohols were dried under vacuum.

Example 14
Synthesis of 1-O-hexadecyl-2-O-methyl-3-O-(3',4',6'-tri-O-benzyl-2-O-methyl-β-D-glucopyranoyl)-sn-gylcerol 1-O-Hexadecyl-2-O-methyl-3-O-(3',4',6'-tri-O-benzyl-β-D-glucopyranosyl-sn-glycerol (149 mg), prepared as described above, was 2-O-methylated as described above, in 97% yield (145 mg). $[α]_D$ −9.7 deg. (c 1.2, chloroform) $^{13}$C-NMR: δ138.89, 138.34, 128.34, 127.93, 127.71, 127.55 (Ph), 103.88 (C-1'), 60.45, 57.88 (CH$_3$O), 31.95, 29.69, 29.52, 29.35, 26.16, 22.68 (CH$_2$), 14.06 (CH3).

Example 15
Synthesis of 1-O-hexadecyl-2-O-methyl-3-O-(3',4',6'-tri-O-benzyl-2-O-methyl-α-D-mannopyranosyl)-sn-gylcerol 1-O-Hexadecyl-2-O-methyl-3-O-(3',4',6'-tri-O-benzyl-α-D-mannopyranosyl -sn-gylcerol (39.6 mg), prepared as described above, was 2-O-methylated as described above, in 98% yield (39 mg). $[α]_D$ +38.3 deg. $^{13}$C-NMR: δ138.89, 138.34, 128.34, 127.93, 127.71, 127.55 (Ph), 98.5 (C-1'), 59.99, 57.80 (CH$_3$O), 31.95, 29.69, 29.52, 29.35, 26.16, 22.68 (CH$_2$), 14.06 (CH$_3$).

Example 16
Xanthates
Synthesis

Sodium hydride (15 mg. 0.62 micromolar) was added to an ice-cold solution of alcohol (150 mg, 0.32 micromolar) and imidazole (4 mg, 0.55 micromolar) in dry THF (5 ml). The mixture was stirred for 1 hour at room temperature under dry nitrogen, and carbon disulfide (0.32 micromolar) was then added. Stirring was continued for 20 minutes, and methyl iodide (2.5 micromolar) was then added. The reaction was monitored by TLC (3:1 hexane:ethyl acetate) and it showed in every case complete conversion of the respective alcohols into xanthated compounds. Methanol was added at 0 deg. C. to quench the excess sodium hydride; solvent was evaporated, and the residue was dissolved in ether. The organic solution was washed with water, dilute hydrochloric acid and then water; the organic layer was then dried (sodium sulfate) and evaporated.

Reduction

A solution of the resulting xanthated compound (100 mg, 0.117 micromolar) in 4 ml of dry toluene was added dropwise to a refluxing solution of tributyl tin hydride (0.31 ml, 1.17 micromolar) in 2 ml dry toluene containing α,α'-azobisisobutyronitrile (AIBN, 5 mg). The reaction was monitored by TLC (4:1 hexane:ethyl acetate), and when it was complete, the solvent was evaporated, and the residue was purified by column chromatography; the column was first eluted with hexane and then with 20:1 hexane:ethyl acetate, 15:1 hexane:ethyl acetate, and 10:1 hexane:ethyl acetate to collect pure deoxygenated 1-O-hexadecyl-2-O-methyl-3-O-(3',4',6'-tri-O-benzyl-2'-deoxy-β-D-arabinopyransoyl)-sn-glycerol or 1-O-hexadecyl-2-O-methyl-3-O-(3',4',6'-tri-O-benzyl-2'-deoxy-β-D-arabinopyransoyl)-sn-glycerol.

1-O-Hexadecyl-2-O-methyl-3-O-(3',4',6'-tri-O-benzyl-2'-deoxy-β-D-arabinopyransoyl)-sn-gylcerol: 80 mg (92%). $[\alpha]_D$ −7.1 deg. $^1$H-NMR: δ7.32–7.18 (m, 15H, 3PhCH$_2$), 4.89 (d, 1H, J=11.0 Hz, OCH$_2$Ph), 4.68 (d, J 11.0 Hz, OCH$_2$Ph), 4.63 (d, 2H, J 11.0 Hz, OCH$_2$Ph), 4.54 (d, 2H, J=11.0 Hz, OCH$_2$Ph), 4.46 (dd, 1H, $J_{1',2e'}$2.0 Hz, $J_{1',2a}$9.5 Hz, H-1'), 3.97 (m, 1H, H-5'), 3.73–3.26 (m, 9H), 3.44 (s, OCH$_3$), 2.36 (ddd, 1H, $J_{2e',3'}$=5.0 Hz, $J_{2'e,2'a}$=12.0 Hz, H-2'e), 1.73–1.43 (m, 5H), 1.25 (s, 26H, CH$_2$), 0.87 (t, 3H, CH$_3$). $^{13}$C-NMR: δ138.46, 128.41, 128.32, 127.97 127.68, 127.51 (Ph), 100.2 (C-1), 57.93 (OCH$_3$), 36.68 (C-2'), 31.94, 29.68, 29.52, 29.35, 26.14, 22.67, 14.06 (CH$_3$).

1-O-Hexadecyl-2-O-methyl-3-O-(3',4',6'tri-O-benzyl-2'-deoxy-α-D-arabinopyransoyl)-sn-gylcerol 82 mg (94%). $[\alpha]_D$ +25.5 deg. $^1$H-NMR: δ7.32–7.15 (m, 15H, 3PhCH$_2$), 4.97 (dd, 1H, H-1'), 4.89 and 4.52 (d, 2H, J=11.0 Hz, OCH$_2$Ph), 4.66 and 4.50 (d, 2H, J 12.0 Hz, OCH$_2$Ph), 4.68 and 4.62 (d, 2H, J=12.0 Hz, OCH$_2$Ph), 3.98 (m, 1H, H-5'), 1.25 (s, 26H, CH$_2$), 0.87 (t, 3H, CH$_3$). $^{13}$C-NMR: δ138.70, 138.59, 138.16, 128.28, 127.58, 97.82 (C-1'), 58.02 (OCH$_3$), 35.45 (C-2'), 31.90, 29.64, 29.48, 29.31, 26.08, 22.64, 14.06 (CH$_3$).

Example 17
Debenzylation

Protected glycosides, see above, were dissolved in 1:1 THF-HOAc, and 1–2 equivalents (in weight) of palladium on charcoal were added. This mixture was degassed under vacuum, then hydrogen was let into the reactor. This process was done three times; the mixture was then stirred at room temperature, under a balloon pressure of hydrogen. The reaction was usually complete in 4–5 hours (TLC 10:1:0.2 ethyl acetate:methanol-water). The catalyst was filtered through a pad of Celite 545, and washed with a large volume of solvent (1:1 THF-HOAc). The solvents were evaporated under vacuum, and trace HOAc was co-evaporated by distilling with toluene.

Deprotected glycosides were purified by column chromatography using a mixture of distilled solvents (10:1 ethyl acetate-methanol). The purified glycosides were then filtered in distilled methanol through lipophilic Sephadex LH-20 to remove low molecular weight impurities, such as salts.

1-O-Hexadecyl-2-O-methyl-3-O-(2'-deoxy-β-D-arabinopyransoyl)-sn-glycerol: 1-O-hexadecyl-2-O-methyl-3-O-(3,4,6-tri-O-benzyl-2'-deoxy-β-D-arabinopyranosyl)-sn-glycerol (30 mg) was debenzylated to give this compound in 96% yield (14 mg). $[\alpha]_D$ −14.7 deg. $^{13}$C-NMR: δ100.3 (C-1'), 78.7 (C-5'), 62.05 (C-6), 58.0 (OCH$_3$) 38.5 (C-2'), 31.95, 29.69, 29.35, 26.11, 22.62 (CH$_2$), 14.09 (CH$_3$). 1-O-Hexadecyl-2-O-methyl-3-O-(2'-deoxy-α-D-arabinopyransoyl)-sn-glycerol: 1-O-hexadecyl-2-O-methyl-3-O-(3',4',6'-tri-O-benzyl-2'-deoxy-α-D-arabinopyranosyl)-sn-glycerol (35 mg) gives the debenzylated compound (21 mg) in 94% yield $[\alpha]_D$ +45.0 deg. $^1$H-NMR: δ4.9 (dd, 1H, $J_{1',2a'}$=2.5 Hz, $J_{1',2e'}$=1.0 Hz, H-1'), 3.93 (m, 1H, H-5'), 3.44 (s, 3H, OCH$_3$), 2.15 (ddd, 1H, $J_{2e',3'}$=4.7 Hz, $J_{2e',2a'}$=11.5 Hz, H-2e'), 1.7 (ddd, 1H, H-2a', 1.25 (s, 26H, CH$_2$), 0.87 (t, 3H, CH$_3$). $^{13}$C-NMR: δ98.05 (C-1'), 79.33, (C-5'), 62.07 (C-6'), 57.94 (OCH$_3$), 37.36 (C-2'), 31.90, 29.64, 29.48, 29.31, 26.06, 22.67 (CH$_2$), 14.06 (CH$_3$). 1-O-Hexadecyl-2-O-methyl-3-O-(2'-methyl-β-D-glucopyransoyl)-sn-glycerol: 142.1 mg of 1-O-hexadecyl-2-O-methyl-3-O-(3',4',6'-tri-O-benzyl-2'-O-methyl-β-D-glucopyransoyl)-sn-glycerol was debenzylated in 96% yield (89 mg) to give the debenzylated form in as a white, amorphous solid. $[\alpha]_D$ −14.7 deg. $^{13}$C-NMR: δ103.64 (C-1'), 62.36 (C-6'), 60.61, 57.89 (OCH$_3$), 31.90, 29.64, 29.48, 29.31, 26.06, 22.67 (CH$_2$), 14.06 (CH$_3$). 1-O-Hexadecyl-2-O-methyl-3-O-(2'-O-methyl-α-D-mannopyransoyl)-sn-glycerol: 1-O-hexadecyl-2-O-methyl-3-O-(3',4',6'-tri-O-benzyl-2-O-methyl-α-D-mannopyransoyl)-sn-glycerol (39 mg) was debenzylated to afford a white amorphous solid (25 mg, 94%). $[\alpha]_D$ +40.0 deg. $^{13}$C-NMR: δ98.89 (C-1'), 79.5 (C-5'), 62.13 (C-6'), 60.1, 58.10 (OCH$_3$), 31.90, 29.64, 29.48, 29.31, 26.06, 22.67 (CH$_2$), 14.06 (CH$_3$). 1-O-Hexadecyl-2-O-methyl-3-O-(α-D-mannopyransoyl)-sn-glycerol: 1-O-hexadecyl-2-O-methyl-3-O-(3',4',6'-tri-O-benzyl-α-D-mannopyranosyl)-sn-glycerol (40 mg) was debenzylated to give a white amorphous solid in 95% yield (25 mg). %). $[\alpha]_D$ +57.2 deg. $^1$H-NMR: δ4.93 (d, 1H, $J_{1',2'}$=1.8 Hz, H-1), 4.10 (m, 1H, H-5'), 1.25 (s, 26H, CH$_2$), 0.87 (t, 3H, CH$_3$).

Example 18
Antiproliferative Effects

The effect of 1-O-hexadecyl-2-O-methyl-3-O-(2'-acetamido-2'-deoxy-β-D-O-glucopyranosyl)-sn-glycerol on the proliferation of MCF-7 breast carcinoma, A549 lung carcinoma, T84 breast carcinoma and A427 colon carcinoma cell lines after 72 h is displayed below (see Table 1). Concentrations that inhibited cell growth by 50% (Gl$_{50}$) in comparison to control (untreated) cultures were 9, 17, 24.5 and >30 micromolar for A549, MCF-7, A427 and T84 cell lines, respectively.

TABLE 1

| Lipid Concentration (μM) | Cell Type | | | |
|---|---|---|---|---|
| | MCF-7 | T84 | A549 | A427 |
| 0 | 100 | 100 | 100 | 100 |
| 5 | 81 ± 8 | 96 ± 10 | 91 ± 9 | 93 ± 12 |
| 10 | 71 ± 6 | 79 ± 12 | 45 ± 3 | 92 ± 6 |
| 15 | 58 ± 5 | 77 ± 13 | 15 ± 2 | 86 ± 10 |
| 20 | 38 ± 2 | 79 ± 16 | 0 | 71 ± 8 |
| 30 | 6 ± 3 | 61 ± 13 | 0 | 24 ± 4 |

Table 2 (see below) shows the effect of 1-O-hexadecyl-2-O-methyl-3-O-(2'-amino-2'-deoxy-βD-glucopyranosyl)-sn-glycerol on the proliferation of the cell lines growing in 10% FBS-supplemented medium. The Gl$_{50}$ values were 6.5, 7, 8.3 and 12.2 micromolar for MCF-7, A427, A549 and T84 cells, respectively. Concentrations of 1-O-hexadecyl-2-O-methyl-3-O-(2'-amino-2'-deoxy-β-D-glucopyranosyl)-sn-glycerol cytotoxic to the cells were determined to be 10.5 micromolar for both A549 and A427 cells, 16 micromolar for MCF-7 and 20 micromolar for T84 cells.

TABLE 2

| Lipid Concentration (μM) | MCF-7 | A549 | A427 | T84 |
|---|---|---|---|---|
| 0 | 100 | 100 | 100 | 100 |
| 5 | 60.60 ± 7.14 | 82.28 ± 4.66 | 68.98 ± 9.25 | 89.71 ± 12.72 |
| 6.5 | 44.05 ± 11.70 | 67.39 ± 6.18 | 49.74 ± 5.16 | — |
| 7.5 | — | — | — | 75.16 ± 10.79 |
| 8.0 | 31.46 ± 5.56 | 45.17 ± 12.06 | 4.29 ± 5.16 | — |
| 10.0 | 14.42 ± 8.39 | 0 | 0 | 64.89 ± 11.56 |
| 12.5 | 3.90 ± 5.75 | 0 | 0 | 39.59 ± 9.50 |
| 15.0 | 0 | 0 | 0 | 15.06 ± 7.23 |
| 20.0 | 0 | 0 | 0 | 0 |

The effect of 1-O-hexadecyl-2-O-methyl-3-O-(2'-amino-2'-deoxy-β-D-glucopyransyl-sn-glycerol (A) and of 1-O-hexadecyl-2-O-methyl-3-O-(2'-acetamido-2'-deoxy-β-D-glucopyranosyl)-sn-glycerol (B) on the growth of the ovarian cancer cell line OVCAR-3 was compared with that of edelfosine (ET-18-O-CH$_3$; C), miltefosine (hexadecylphosphocholine, D), and erucylphosphocholine (E) (see Table 3, below). The Gl$_{50}$ value for the glycolipids were 12 micromolar for A and 4 micromolar for B, while for the phospholipids, Gl$_{50}$'s were 24 micromolar for C and >30 micromolar for D and E.

TABLE 3

| Lipid Concentration (μM) | A | B | C | D | E |
|---|---|---|---|---|---|
| 0 | 100 | 100 | 100 | 100 | 100 |
| 5 | 42.9 ± 13.4 | 68.8 ± 5.8 | 105.8 ± 8.5 | 93.8 ± 16.5 | 104.0 ± 12.2 |
| 10 | 7.7 ± 2.3 | 52.9 ± 3.9 | 77.5 ± 1.0 | 90.3 ± 11.3 | 102.3 ± 16.1 |
| 15 | 0 | 34.6 ± 7.3 | 70.7 ± 9.9 | 67.4 ± 14.5 | 98.6 ± 7.8 |
| 20 | — | 26.0 ± 10.9 | 68.7 ± 13.6 | 62.3 ± 10.7 | 90.2 ± 6.6 |
| 30 | — | 4.7 ± 4.8 | 20.4 ± 8.1 | 67.2 ± 12.5 | 60 ± 10.7 |

The Gl$_{50}$ values for edelfosine (1), 2'-deoxy-β-D-arabinopyranosyl (2), 2'-deoxy-α-D-arabinopyranosyl (3), 2-O-methyl-β-D-glucopyranosyl (4), 2'-O-methyl-β-D-mannopyranosyl (5) and α-D-mannopyransoyl (6) on A-549, MCF-7, Lewis Lung, MCF-7/Adr (adriamycin-resistant), P388, P-388/Adr, L1210 and L1210/vmdr cells were determined and are set forth below (see Table 4) as the concentration (micromolar) of lipid required to inhibit the growth of fifty percent of the cells in culture.

TABLE 4

| | Cell Line | | | | | |
|---|---|---|---|---|---|---|
| | 1 | 2 | 3 | 4 | 5 | 6 |
| A549 | 5.05 ± 0.80[a] | 9.90 ± 0.99 | 19.65 ± 0.07 | 18.30 ± 0.14 | 15.55 ± 0.07 | 18.10 ± 0.14 |
| MCF7 | 9.66 ± 2.50[a] | 6.93 ± 0.12 | 24.45 ± 0.64 | 23.05 ± 0.64 | 18.20 ± 0.00 | 21.70 ± 0.57 |
| MCF7/adr | 30.35 ± 5.07[b] | 12.85 ± 0.85 | 24.40 ± 0.42 | 21.75 ± 0.63 | 18.55 ± 0.07 | 23.30 ± 0.71 |
| HT29 | 2.20 ± 0.27[b] | 7.59 ± 0.23 | 29.60 ± 0.28 | — | 20.00 ± 0.28 | 23.20 ± 0.85 |
| Lewis Lung | 30.24 ± 6.32[c] | 11.05 ± 0.49 | — | 26.00 ± 0.71 | — | — |
| P388 | 4.33 ± 1.37[d] | 12.65 ± 0.78 | — | 18.10 ± 1.13 | — | — |
| P388/adr | 6.39 ± 2.43[d] | 10.25 ± 0.34 | — | 29.30 ± 5.66 | — | — |
| L1210 | 3.32 ± 1.68[c] | 7.02 ± 0.49 | 18.75 ± 0.49 | — | 15.45 ± 0.35 | 16.20 ± 0.99 |
| L1210/vmdr | 10.99 ± 6.36[c] | 7.09 ± 0.33 | 26.95 ± 1.06 | — | 16.50 ± 1.13 | 18.90 ± 0.00 |

Gl$_{50}$ values are given as the mean ± standard deviation; the Gl$_{50}$ value from each experiment "n" was generated from three individual wells on two separate plates (six total wells); n=1 for compounds 3–6; n=2 for most cell lines treated with compound 2 [a]n=3; [b]n=2; [c]n=6; [d]n=8.

What is claimed is:

1. An etherlipid having the formula:

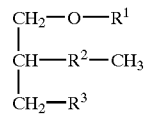

wherein:

R$^1$ is a group having the formula —Y$^1$Y$^2$;

Y$^1$ is a group having the formula —(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$ and the sum of n1+2n2+n3+2n4+n5+2n6+n7+2n8+n9 is an integer of from 3 to 23, n1 is equal to zero or an integer of from 1 to 23, n3 is equal to zero or an integer of from 1 to 20, n5 is equal to zero or an integer of from 1 to 17, n7 is equal to zero or an integer of from 1 to 14, n9 is equal to zero or an integer of from 1 to 11, and each of n2, n4, n6 and n8 is independently zero or 1;

Y$^2$ is CH$_3$, CO$_2$H or OH;

R$^2$ is O, S, NH, —OC(O)— or NHCO;

R$^3$ is a group having the formula

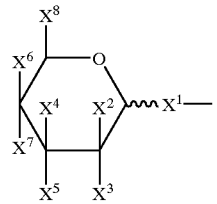

wherein:

X$^1$ is O or S;

X$^2$ is H, OH, NH$_2$, NHCH$_3$, N(CH$_3$)$_2$, OCH$_3$, NHCOCH$_3$, F or Cl;

X$^3$ is H, OH, NH$_2$, NHCH$_3$, N(CH$_3$)$_2$, OCH$_3$, F or Cl, provided that when X$^2$ is H, X$^3$ is H, NH$_2$, NHCH$_3$, OCH$_3$, F or Cl;

$X^4$ is H, OH, $OPO_3^{3-}$ or $OSO_3^{2-}$ and
$X^5$ is H, OH, $NH_2$, $NHCH_3$ or $N(CH_3)_2$;
each of $X^6$ and $X^7$ is H, OH, —$OX^9$, $OPO_3^{3-}$ or $OSO_3^{2-}$;
$X^8$ is $CH_2OH$ when the sugar is unmodified at the C-6 position, or a group having the formula $COOX^{10}$, when the sugar is modified at this position;
$X^9$ is a tetrose, pentose, hexose or heptose sugar;
$X^{10}$ is H, $CH_3$ or a group having the formula $Y^1Y^2$; and
wherein no more than two of $X^2$, $X^3$, $X^4$, $X^5$, $X^6$ and $X^7$ are OH and no more than two of $X^2/X^3$, $X^4/X^5$ and $X^6/X^7$ are H/OH or OH/H when $X^8$ is $CH_2OH$.

2. The etherlipid of claim 1, wherein $R^1$ is a group having the formula $Y^1CH_3$.

3. The etherlipid of claim 2, wherein $R^1$ is a group having the formula $(CH_2)_{n1}CH_3$.

4. The etherlipid of claim 3, wherein $R^1$ is $(CH_2)_{15}CH_3$ or $(CH_2)_{17}CH_3$.

5. The etherlipid of claim 1, wherein $R^2$ is O.

6. The etherlipid of claim 1, wherein $R^3$ is the alpha anomeric form.

7. The etherlipid of claim 1, wherein $R^3$ is the beta anomeric form.

8. The etherlipid of claim 1, wherein $X^1$ is O.

9. The etherlipid of claim 1, wherein $X^4$ is OH, $X^5$ is H, $X^6$ is H, $X^7$ is OH and wherein $X^2$ is H and $X^3$ is $NH_2$, H or $OCH_3$ or wherein $X^3$ is H and $X^2$ is OH, H or $OCH_3$.

10. The etherlipid of claim 1, wherein $R^1$ is $(CH_2)_{15}CH_3$, $R^2$ is O and $X^1$ is O.

11. The etherlipid of claim 10, wherein $X^4$ is OH, $X^5$ is H, $X^6$ is H, $X^7$ is OH and wherein $X^2$ is H and $X^3$ is $NH_2$, H or $OCH_3$ or wherein $X^3$ is H and $X^2$ is OH, H or $OCH_3$.

12. The etherlipid of claim 10, wherein $X^2$ is H, $X^3$ is OH, $X^4$ is OH, $X^5$ is H, $X^6$ is H, $X^7$ is OH and $X^8$ is $COOX^{10}$ and wherein $X^{10}$ is $CH_3$ or a group having the formula $Y^1Y^2$.

13. A pharmaceutical composition comprising the etherlipid of claim 1 and a pharmaceutically acceptable medium.

14. The composition of claim 13, wherein the pharmaceutically acceptable medium comprises a lipid carrier and wherein the etherlipid is associated with the carrier.

15. The composition of claim 14, wherein the lipid carrier is a fatty acid, phospholipid, micelle, lipid complex, liposome or lipoprotein.

16. A method of treating an animal afflicted with a cancer which comprise administering an anticancer-effective amount of the composition of claim 13 to the animal.

17. The method of treating an animal as described in claim 16, wherein the composition comprises a liposome.

18. The method of treating an animal as described in claim 16, further comprising administering an additional bioactive agent to the animal.

19. The etherlipid of claim 1, is 1-O-hexadecyl-2-O-methyl-3-O-(2'-amino-2'-deoxy-β-D-glucopyranosyl)-sn-glycerol.

* * * * *